(12) United States Patent
Sevenier et al.

(10) Patent No.: US 11,293,039 B2
(45) Date of Patent: Apr. 5, 2022

(54) METHOD FOR PRODUCING ORGANIC ACID SALTS FROM FERMENTATION BROTH

(71) Applicant: METABOLIC EXPLORER, Saint Beauzire (FR)

(72) Inventors: Antoine Sevenier, Oont du chateau (FR); Cédric Colomb, Ennezat (FR); Benjamin Martin, Clermont-ferrand (FR)

(73) Assignee: METABOLIC EXPLORER, Saint Beauzire (FR)

( * ) Notice: Subject to any disclaimer, the term of this patent is extended or adjusted under 35 U.S.C. 154(b) by 0 days.

(21) Appl. No.: 16/652,812

(22) PCT Filed: Oct. 1, 2018

(86) PCT No.: PCT/EP2018/076648
§ 371 (c)(1),
(2) Date: Apr. 1, 2020

(87) PCT Pub. No.: WO2019/068642
PCT Pub. Date: Apr. 11, 2019

(65) Prior Publication Data
US 2020/0231995 A1 Jul. 23, 2020

(30) Foreign Application Priority Data
Oct. 2, 2017 (EP) .................................... 17306317

(51) Int. Cl.
*C12P 7/54* (2006.01)
*C12P 7/42* (2006.01)
*C12P 7/52* (2006.01)
*C12P 7/56* (2006.01)

(52) U.S. Cl.
CPC .................. *C12P 7/54* (2013.01); *C12P 7/42* (2013.01); *C12P 7/52* (2013.01); *C12P 7/56* (2013.01)

(58) Field of Classification Search
CPC ...................................................... C12P 7/52
See application file for complete search history.

(56) References Cited

U.S. PATENT DOCUMENTS

| | | | |
|---|---|---|---|
| 3,720,584 A | 3/1973 | Yamada et al. | |
| 4,490,295 A | 12/1984 | Fleming et al. | |
| 2004/0048344 A1 | 3/2004 | Baldenius et al. | |
| 2004/0077057 A1 | 4/2004 | Beck et al. | |
| 2008/0311640 A1* | 12/2008 | Cox | C12M 47/18 435/168 |

FOREIGN PATENT DOCUMENTS

| | | |
|---|---|---|
| CN | 101475464 A | 8/2009 |
| EP | 0 350 355 A1 | 1/1990 |
| EP | 1094054 A1 | 4/2001 |
| WO | WO 2013/169447 A1 | 11/2013 |

OTHER PUBLICATIONS

Park et al., J of Microbiology and Biotechnology, 1993, 3(4):266-269.*
Anderson et al., "Growth Requirements of Virus-Resistant Mutants of *Escherichia coli* Strain "B"," Proc. N. A.S., vol. 32, 1946, pp. 120-128.
Pacaud et al., "Methanol Metabolism by Eubacterium limosum B2: Effects of pH and Carbon Dioxide on Growth and Organic Acid Production," Current Microbiology, vol. 12, 1985, pp. 245-250 (2 pages).
Schafer et al., "Automated Sampling Device for Monitoring Intracellular Metabolite Dynamics," Analytical Biochemistry, vol. 270, 1999, pp. 88-96.
Zhao et al., "A quantitative metabolomics study of high sodium response in Clostridium acetobutylicum ATCC 824 acetone-butanol-ethanol (ABE) fementation," Scientific Report, vol. 6, No. 28307, Jun. 20, 2016, 13 pages.
International Search Report issued in PCT/EP2018/076648 (PCT/ISA/210), dated Jan. 16, 2019.
Written Opinion of the International Searching Authority issued in PCT/EP2018/076648 (PCT/ISA/237), dated Jan. 16, 2019.

* cited by examiner

*Primary Examiner* — Bin Shen
(74) *Attorney, Agent, or Firm* — Bikch, Stewart, Kolasch & Birch, LLP (57) ABSTRACT

The invention relates to a method for producing salts of butyric acid, lactic acid, propionic acid, valeric acid, acetic acid, glycolic acid, sorbic acid, fumaric acid, formic acid, malic acid, tartaric acid, citric acid, derivatives of said organic acids and mixtures thereof, comprising at least the successive steps of: •i) culturing a microorganism in an appropriate culture medium comprising a carbon source and a nitrogen source, during a sufficient time to obtain a fermentation broth comprising the organic acid(s); •ii) pretreating said fermentation broth comprising at least clarification of the fermentation broth and separation of organic acids by evaporation of the clarified fermentation broth and then condensation of the volatile fraction containing organic acids (CVAF); •v) adding inorganic bases to said CVAF •vii) eliminating the remaining water of the CVAF, and recovering the organic acid salts.

11 Claims, 5 Drawing Sheets

Figure 5

METHOD FOR PRODUCING ORGANIC ACID SALTS FROM FERMENTATION BROTH

FIELD OF THE INVENTION

The present invention relates to a method for the fermentative production of organic acid salts with high purity from a fermentation broth.

BACKGROUND OF THE INVENTION

Organic acids are defined as compounds build on a carbon skeleton, containing a functional group with acidic properties, usually weaker than mineral acids.

Organic acids are widely distributed in nature as normal constituents of microorganisms, plants or animal tissues. They are produced during metabolism of carbohydrates, through microbial fermentation, and during degradation of amino acids and other organic compounds.

Availability of organic acids and derivatives thereof is of great economic interest, since several industrial uses have been identified.

Organic acid such as succinic acid and lactic acid may be used to generate biodegradable polymers. Glycolic acid is used in the preparation of polyglycolic acid and other biocompatible copolymers (e.g. PLGA).

Organic acids are used in food preservation because of their antibacterial activity.

Moreover, organic acids are successfully used, instead of antibiotics and without the same health concerns, in animal feeding. Following the European ban of antibiotic growth promoters in 2006, the use of organic acids in animal nutrition has gained significant importance in the feed industry. Among organic acids, butyric acid is of particular importance, due to its significant ability to reduce pathogenic bacterial colonization.

Organic acids can be either isolated from natural sources, produced by chemical synthesis, or obtained by microbiological fermentation.

Advantageously, microbiological fermentation may allow the production of specific enantiomers of organic acid (L or D) after genetic engineering of the microorganisms, these isolated isomers (L or D) each exhibiting specific characteristics, as for example the isomers L-lactic acid and D-lactic acid.

Genetic modifications of the microorganisms have also been used in order to improve the yield of production of organic acids.

Also, improvements in the culture process have been made, for example control of the pH of the fermentation medium for the production of glycolic acid (WO 2011/036213).

In the goal to optimize the recovery of the produced organic acids, different techniques have been developed for the purification and recovery of these organic acids.

EP 1 094 054 and EP 350 355 disclose methods for separation and purification of lactic acid and butyric acids, respectively, produced by fermentation.

U.S. Pat. No. 4,490,295 discloses a process for producing clavulanic acid and lithium salts thereof, from a fermentation broth of *Streptomyces clavuligerus*. It has been observed that isolation of the clavulanic acid is greatly facilitated if it is previously converted into its salt, lithium clavulanate, that can be precipitated with little co-precipitation of impurities.

Organic acid salts are combined forms of the conjugate base of an organic acid with one or more cations, electrically neutral.

Organic acid salts are easier to recover than their corresponding organic acids, and are also usable as such as additives for animal feed.

US 2004/0048344 is related to a process for producing D-pantothenic acid salts comprising the following steps:
  Fermentation of a specific microorganism (preferably from the genus *Bacillus*);
  Passing the fermentation broth through a cation exchanger, free pantothenic acid being formed from the separation with cations;
  Adding a calcium base and/or magnesium base to adjust the pH to 3-10, thereby obtaining calcium and/or magnesium pantothenate salts;
  Subjecting the solution to drying and/or formulation.

US 2004/0077057 discloses a process for producing D-pantothenic acid salts comprising the following steps:
  Fermentation of a specific microorganism (preferably from the genus *Bacillus*);
  Passing the fermentation broth through an anion exchanger;
  Eluting the D-pantothenate bound to the anion exchanger using solution containing salts (calcium and/or magnesium) or an HCL solution;
  Subjecting the eluate to drying and/or formulation.

All these techniques involve a direct treatment of the fermentation broth. However, organic acids are diluted in the fermentation medium, i.e. they are present in a concentration comprised between about 0.1% and about 10%, and therefore at the end of the process, the yields of recovered organic acid salts are low.

Processes comprising a step of clarification of the fermentation broth, for example by ultrafiltration, have been previously reported.

The U.S. Pat. No. 3,720,584 relates to a process for producing carboxylic acid salts, in particular lactic acid salts, from a clarified fermentation broth of microorganisms of the genus *Arthrobacter, Alcaligenes* or *Fusarium*. Nevertheless, this process does not include a step of evaporation of the clarified fermentation broth, and therefore the organic acids are still highly diluted in the treated medium.

Moreover, patent applications CN101475464 and WO 2013/169447 disclose processes for producing succinic acid salts from a fermentation broth, comprising a step of clarification of said broth. Nevertheless, these processes do not relate to the production of organic acid salts chosen among the group consisting of: salts of butyric acid, lactic acid, propionic acid, valeric acid, acetic acid, glycolic acid, sorbic acid, fumaric acid, formic acid, malic acid, tartaric acid, citric acid, derivatives and mixtures thereof.

Finally, with the already known processes, the purity of recovered organic acid salts is poor, since the level of impurities and by-products in the non-treated fermentation medium is important.

The present application is aimed to improve the yield and the purity of organic acid salts chosen among salts of butyric acid, lactic acid, propionic acid, valeric acid, acetic acid, glycolic acid, sorbic acid, fumaric acid, formic acid, malic acid, tartaric acid, citric acid, derivatives of said organic acids and mixtures thereof, recovered from fermentation broths.

SUMMARY OF THE INVENTION

The present invention relates to a method for producing organic acid salts comprising at least the successive steps of:

i) culturing a microorganism in an appropriate culture medium comprising a carbon source and a nitrogen source, during a sufficient time to obtain a fermentation broth comprising organic acids;
ii) pre-treating said fermentation broth with at least the following steps:
   a. clarification of the fermentation broth;
   b. optionally, adjustment of the pH of the clarified fermentation broth; and
   c. separation of organic acids by evaporation of the clarified fermentation broth and then condensation of the volatile fraction containing said organic acids, hereafter designated as the condensed volatile acids fraction (CVAF);
iii) optionally, passing the CVAF over a cation exchanger able to bind the ammonium cations;
iv) optionally, passing the CVAF or the cationic resin treated fraction over an anion exchanger able to bind the conjugate bases of the organic acids;
v) adding inorganic bases to said CVAF or to said cationic resin treated fraction or to said anion exchanger to eluate the bound conjugate bases;
vi) eliminating the remaining water of the CVAF or of the cationic resin treated fraction or of the eluate, and recovering the formed organic acid salts,
wherein the organic acid salts are chosen among the group consisting of: salts of butyric acid, lactic acid, propionic acid, valeric acid, acetic acid, glycolic acid, sorbic acid, fumaric acid, formic acid, malic acid, tartaric acid, citric acid, derivatives of said organic acids and mixtures thereof.

The herein disclosed process for recovery of organic acid salts from a fermentation broth interestingly comprises a step (ii) of pre-treatment of the fermentation broth: during this pre-treatment, the fermentation broth is (a) clarified, (b) optionally, the pH is adjusted and (c) submitted to a step of evaporation/condensation that allows the separation of the volatile organic acids and the elimination of waste material, in particular of salts and heavy compounds (inorganic salts, sugars . . . ).

These pre-treatment steps allow the concentration of organic acids in the solution, before performing the steps (v) and (vi) of generation of organic acid salts.

Use of these pre-treatment steps of the fermentation broth has significantly increased the yield and purity of the recovered organic acids salts. Moreover this process allows increasing the profitability of other fermentation processes: the method for producing organic acid salts according to the invention allows the use of waste waters, originating from other processes, these waste waters becoming a valuable product.

The present invention also relates to a mixture of at least two organic acid salts such as obtained by the method as described above.

This mixture of at least two organic acid salts may in particular be characterized by the fact that butyric acid salts and derivative thereof are the major components of said mixture.

DETAILED DESCRIPTION OF EMBODIMENTS OF THE INVENTION

Before describing the present invention in detail, it is to be understood that the practice of the present invention employs, unless otherwise indicated, conventional microbiological and chemical purification techniques within the skill of the art. Such techniques are well known to the skilled worker, and are fully explained in the literature.

Moreover, in the claims and in the description of the invention, except where the context requires otherwise due to express language or necessary implication, the word "comprise", "contain", "involve" or "include" or variations such as "comprises", "comprising", "containing", "involved", "includes", "including" are used in an inclusive sense, i.e. to specify the presence of the stated features but not to preclude the presence or addition of further features in various embodiments of the invention.

In the claims and description, the terms "process" and "method" are used interchangeably.

The present invention relates to a method for producing organic acid salts comprising at least the successive steps of:
i) culturing a microorganism in an appropriate culture medium comprising a carbon source and a nitrogen source, during a sufficient time to obtain a fermentation broth comprising organic acids;
ii) pre-treating said fermentation broth with at least the following steps:
   a. clarification of the fermentation broth;
   b. optionally, adjustment of the pH of the clarified fermentation broth; and
   c. separation of organic acids by evaporation of the clarified fermentation broth and then condensation of the volatile fraction containing said organic acids, hereafter designated as the condensed volatile acids fraction (CVAF);
iii) optionally, passing the CVAF over a cation exchanger able to bind the ammonium cations;
iv) optionally, passing the CVAF or the cationic resin treated fraction over an anion exchanger able to bind the conjugate bases of the organic acids;
v) adding inorganic bases to said CVAF or to said cationic resin treated fraction or to said anion exchanger to eluate the bound conjugate bases;
vi) eliminating the remaining water of the CVAF (condensed volatile acids fraction) or of the cationic resin treated fraction or of the eluate, and recovering the formed organic acid salts,
wherein the organic acid salts are chosen among the group consisting of: salts of butyric acid, lactic acid, propionic acid, valeric acid, acetic acid, glycolic acid, sorbic acid, fumaric acid, formic acid, malic acid, tartaric acid, citric acid, derivatives of said organic acids and mixtures thereof.

Organic Acids

The term "organic acid" designates generally organic compounds with acidic properties. This term includes in particular carboxylic acids and sulfonic acids, containing the group —$SO_2OH$.

The most common organic acids are carboxylic acids, characterized with the presence of a carboxyl group (—COOH) composed of two functional groups: a hydroxyl group (—OH) that is bonded to a carbonyl group (C=O).

Organic acids are written in a condensed form R—COOH. Carboxylic acids include aliphatic, aromatic and cycloaliphatic carboxylic acids, depending on the structure of the carbon skeleton (R).

Organic acids commonly found in fermentation broth are the following: lactic acid, acetic acid, succinic acid, propionic acid, butyric acid, methyl butyric acid, hydroxybutyric acid, aminobutyric acid (in particular GABA, gamma-aminobutyric acid), valeric acid, formic acid, aspartic acid, fumaric acid, oxalic acid, orotic acid, ketoglutaric acids, citric acid, glutamic acid, glyoxylic acid, glycolic acid, pyruvic acid, malic acid, sorbic acid and tartaric acid.

Organic acids are present in aqueous solution under two chemical forms: AH and A-. This A- form is named the "conjugate base" of the acid AH. For example, for the acetic acid AH, the conjugate base A- will be designated as acetate.

In the present application, it is understood that when an organic acid is designated as "acid", it designates the combination in equilibrium, in an aqueous solution, of both forms AH and A-. The AH form is designated as "the associate or protonated form" of the acid and the A- form is designated as the conjugate base or "the dissociate or deprotonated form" of the acid. Proportion of AH form versus A- form is depending on pH value of the solution and pKa of the organic acid A.

The conjugate base, negatively charged, tends to associate with positively charged ions (cations) such as sodium ($Na^+$), ammonium ($NH_4^+$), calcium ($Ca^{2+}$), potassium ($K^+$) and magnesium ($Mg^{2+}$) ions.

Salts of organic acid are defined as a combination, electrically neutral, of the conjugate base of an organic acid and of one or more cations.

In one embodiment of the present application, the method for producing organic acid salts is a method for producing carboxylic acid salts.

In another embodiment of the present application, the method is a method for producing organic acid salts chosen among the group consisting of: salts of lactic acid, acetic acid, succinic acid, propionic acid, butyric acid, methyl butyric acid, hydroxybutyric acid, aminobutyric acid (in particular GABA, gamma-aminobutyric acid), valeric acid, formic acid, aspartic acid, fumaric acid, oxalic acid, orotic acid, ketoglutaric acids, citric acid, glutamic acid, glyoxylic acid, glycolic acid, pyruvic acid, malic acid, sorbic acid, tartaric acid, derivatives of said organic acids and mixtures thereof.

The method of the invention is specifically intended for the production of organic acid salts chosen among the group consisting of: salts of butyric acid, lactic acid, propionic acid, valeric acid, acetic acid, glycolic acid, sorbic acid, fumaric acid, formic acid, malic acid, tartaric acid, citric acid, derivatives of said organic acids and mixtures thereof.

Butyric acid (No. CAS 107-92-6) is produced as end-product of a fermentation process solely performed by obligate anaerobic bacteria, either wild-type or recombinant. Examples of butyrate-producing species of bacteria are the following:
  Clostridium acetobutylicum
  Clostridium butyricum
  Clostridium kluyveri
  Clostridium pasteurianum
  Faecalibacterium prausnitzii
  Fusobacterium nucleatum
  Butyrivibrio fibrisolvens
  Eubacterium limosum Lactic acid occurs in two isomeric forms: isomer L (+), No. CAS 79-33-4, isomer D (-), No. CAS 10326-41-7, and as a racemic mixture: DL-lactic acid, No. CAS 50-21-5. Lactic acid producing bacteria are broadly categorized into two types:
  Hetero-fermentative bacteria that produce other products besides lactic acid, and
  Homo-fermentative bacteria that are specialised for exclusive production of lactic acid, such as Lactobacillus sp.

Propionic acid (CAS No. 79-09-4) and its salts propionates or propanoates are naturally occurring compounds. In industry, propionic acid is mainly produced chemically, by the hydrocarboxylation of ethylene, or by the aerobic oxidation of propionaldehyde. Propionic acid is also produced biologically under the form of a coenzyme A ester, propionyl-CoA, from the metabolic breakdown of certain fatty acids, and also from the degradation of some amino acids. Bacteria of the genus Propionibacterium produce propionic acid as the end-product of their anaerobic metabolism.

Valeric acid (CAS No. 109-52-4, also called pentanoic acid), presents the chemical formula $C_5H_{10}O_2$. Although little is known about the possibility to produce it by fermentation, the patent application WO 2012/030860 reports the biosynthesis of its derivative levulinic acid, also known as 4-oxopentanoic acid, with specific enzymes.

Acetic acid (systematically named ethanoic acid, No. CAS 64-19-7) can be produced both synthetically and by bacterial fermentation with aerobic, nitrogen-fixing bacteria. Among numerous strains able to produce acetic acid, Gluconobacter, Eubacterium limosum and Acetobacter (A. aceti, A. peroxidans, A. pasteurianus), a group of Gram-negative bacteria comprised in the family Acetobacteraceae, might be cited.

Glycolic acid (No. CAS 79-14-1) is produced by chemical synthesis, is purified from natural sources, or is obtained by bioconversion. It also can be obtained from fermentation of the yeasts Saccharomyces cerevisiae and Kluyveromyces lactis. Methods for producing glycolic acid by fermentation from renewable resources using bacteria (E. coli, C. glutamicum) or yeast (S. cerevisiae) are disclosed in patent applications from the Applicant (WO 2007/141316, WO 2010/108909, WO 2011/157728, WO 2011/036213, WO 2012/025780).

Sorbic acid (No. CAS 110-44-1), or 2,4-hexadienoic acid, is used as a food preservative. It was first isolated from the unripe berries of the rowan tree (Sorbus aucuparia).

Fumaric acid (No. CAS 110-17-8), or trans-butenedioic acid, is used as a food acidulant. It is found naturally in fumitory (Fumaria officinalis), bolete mushrooms, lichen, and Iceland moss. Fumaric acid is an intermediate in the citric acid cycle: it is formed by the oxidation of succinate, and is then converted into malate. Fumaric acid is also a product of the urea cycle. Therefore, many microorganisms produce fumaric acid, and production by fermentation, for example by Rhizopus species, is currently considered.

Formic acid (No. CAS 64-18-6), systemically named methanoic acid, occurs widely in nature as its conjugate base formate. It may be produced by hydrothermal oxidation of biomass material, such as glucose, starch and cellulose. Moreover, by fermentation of Acetobacterium woodii, formate may be obtained by hydrogenation of $CO_2$ with a carbon dioxide reductase enzyme.

Malic acid (No. CAS 617-48-1 and 6915-15-7) is currently used mainly as an acidulant and taste enhancer in the beverage and food industry. When added to food products, malic acid is designated by E number E296. Malic acid is the main acid in many fruits. It contributes to the sourness of green apples and rhubarb. Malic acid occurs naturally in all fruits and many vegetables, and is generated in fruit metabolism. Malic acid is an intermediate in the Calvin cycle and in the citric acid cycle. It can also be formed from pyruvate via anaplerotic reactions. In 1924, malic acid was identified as a product of yeast fermentation. Since then, malic acid production has been observed for a wide range of microorganisms. Fermentative production of malic acid has been most successfully demonstrated with *Aspergillus flavus*, *Saccharomyces cerevisiae*, and *Zygosaccharomyces rouxii*.

Tartaric acid (No. CAS 526-83-0) occurs naturally in many plants, most notably in grapes, and is used as an acidulant in foods. It may be produced by fermentation, in particular with microorganisms belonging to genus *Pseudomonas, Agrobacterium*, or *Rhizobium*.

Citric acid (No. CAS 77-92-9) was first isolated from lemon juice. Citric acid is mainly used in food industry because of its pleasant acid taste and its high solubility in water. Citric acid is the most important organic acid produced in tonnage and is extensively used in food and pharmaceutical industries. It is produced mainly by fermentation using *Aspergillus niger, Saccharomycopsis* sp or *Candida* sp. from different sources of carbohydrates. It may also be produced by fermentation of the yeast *Yarrowia lipolytica* and related species.

In the meaning of the invention, the term "derivatives of organic acids" designate chemical compounds having a carbon skeleton presenting the same number of carbon atoms and the same acyl function than the considered organic acid, but whose chemical formula is modified:
   by replacement of the hydroxyl group with substituents, such as an halogen atom, an alkoxyl, and amino and an acyloxy group; or
   by addition of other functional groups such as hydroxyl groups.
Common classes of organic acid derivatives include:
alpha-hydroxy acids (AHA), wherein a carboxylic acid comprises a hydroxyl group on the adjacent carbon of the carboxyl group;
acyl halide, wherein the hydroxyl has been replaced with an halogen (F, Cl, Br or I);
anhydride, wherein two organic acids are linked with an oxygen atom between the two acyl groups;
ester, wherein the hydroxyl group has been replaced with an alkoxyl group; and
amide, wherein the hydroxyl group has been replaced with a group $NH_2$ or $NR_2$, R being hydrogen or an alkyl.

It is understood that the process of the invention does not comprise a selection step of particular organic acid salts. Therefore, the produced organic acid salts are recovered under the form of a mixture of at least two different organic acid salts and derivatives thereof. Nevertheless, there are generally one or two major compounds in the mixture. This point will be discussed more extensively below.

Step (i) of the Process: Culture of a Microorganism

The term "microorganism", as used herein, refers to a bacterium, a yeast or a fungus. The microorganism may be selected among bacteria belonging to the families Eubacteriaceae, Enterobacteriaceae, Bacillaceae, Clostridiaceae or Corynebacteriaceae. Alternatively, the microorganism may be selected among yeast belonging to the Saccharomycetaceae family. Alternatively, the microorganism may be selected among fungi belonging to the Ascomycota family.

In one embodiment, the microorganism cultivated in the method of the invention is a bacterium, preferentially chosen among the group of species consisting of: *Escherichia coli*, *Bacillus subtilis*, *Corynebacterium glutamicum*, *Clostridium acetobutylicum*, *Clostridium pasteurianum*, and *Eubacterium limosum*.

Preferentially, the microorganism cultivated in the method of the invention is either from the species *Clostridium acetobutylicum*, *Eubacterium limosum* or *Escherichia coli*.

In a specific embodiment of the invention, the cultivated microorganism is *Clostridium acetobutylicum*.

In one embodiment, the microorganism cultivated in the method of the invention is a yeast, preferentially chosen among the group of species consisting of: *Saccharomyces cerevisiae, Pichia kudriavzevii* and *Kluyveromyces lactis*.

In one embodiment, the microorganism cultivated in the method of the invention is a fungus, preferentially from *Aspergillus niger* species.

According to the invention, the cultivated microorganism is a wild-type microorganism or a genetically-modified, recombinant microorganism.

Preferably the microorganism cultivated at the step i) of the method according to the invention is the sole microorganism in the culture, which means that a single strain of microorganism is fermented.

According to the invention the terms "fermentative production", "culture" or "fermentation" are used interchangeably to denote the growth of microorganism. This growth is generally conducted in fermenters with an appropriate culture medium adapted to the microorganism, and containing at least one carbon source and one source of nitrogen.

An "appropriate culture medium" designates a medium (e.g., a sterile, liquid media) comprising nutrients essential or beneficial to the maintenance and/or growth of the cell such as carbon sources or carbon substrates, nitrogen sources, for example, peptone, yeast extracts, meat extracts, malt extracts, urea, ammonium sulphate, ammonium chloride, ammonium nitrate and ammonium phosphate; phosphorus sources, for example, monopotassium phosphate or dipotassium phosphate; trace elements (e.g., metal salts), for example magnesium salts, cobalt salts and/or manganese salts; as well as growth factors such as amino acids and vitamins.

The term "carbon source" or "carbon substrate" or "source of carbon" according to the present invention denotes any source of carbon that can be used by those skilled in the art to support the normal growth of a microorganism, including monosaccharides (such as glucose, galactose, xylose, fructose or lactose), oligosaccharides, disaccharides (such as sucrose, cellobiose or maltose), polyols such as glycerol or glycerine, molasses, starch or its derivatives, hemicelluloses and combinations thereof. An especially preferred simple carbon source is glucose. Another preferred simple carbon source is sucrose.

The carbon source can be derived from renewable feed-stock. Renewable feed-stock is defined as raw material required for certain industrial processes that can be regenerated within a brief delay and in sufficient amount to permit its transformation into the desired product. As an example, vegetal biomass, treated or not, is a renewable feed-stock that can be used as carbon source.

The terms "source of nitrogen" corresponds to either an ammonium salt or ammoniac gas. The nitrogen source is supplied in the form of ammonium, ammoniac or urea.

According to the invention, the terms "fermentative medium", "medium", "fermentative broth", "fermentation broth" and "broth" are used interchangeably and designate the fermentative medium comprising cultivated microorganisms. These terms mean that the culture of microorganisms has been performed during a sufficient time for the microorganisms to grow and synthesize organic acids.

According to the invention, the phrase "a sufficient time to obtain a fermentation broth comprising organic acids" designate a culture time sufficient for the microorganisms to grow significantly, in particular to replicate and colonize all the fermentation medium. This time will depend on the nature of the microorganism, on the volume of the culture, and on other culture conditions (temperature, shaking, pH). This sufficient time can be determined by the man skilled in the art of microorganism culture. For example, for a culture volume of 1000 liters, a sufficient time is generally about 2 days of culture in optimal conditions of culture for *Escherichia coli*, and is generally about 7 days of culture in optimal conditions of culture for *Clostridium acetobutylicum*.

In particular the microorganisms are fermented at a temperature between 20° C. and 55° C., preferentially between 25° C. and 40° C., and more specifically about 35° C. for *Clostridium*, about 37° C. for *Eubacterium*, and about 37° C. for *E. coli*. For heat-inducible strains, the culture temperature is advantageously about 30° C., at some points of the process.

For *E. coli*, the culture medium can be of identical or similar composition to an M9 medium (Anderson, 1946), an M63 medium (Miller, 1992); or a medium such as defined in (Schaefer et al., 1999).

For *Clostridium acetobutylicum*, the culture medium can be of identical or similar composition to a CGM (Clostridial Growth Medium) or a RCM (Reinforced Clostridial Medium) such as defined in (Zhao et al., 2016).

For *Eubacterium limosum*, the culture medium can be of identical or similar composition to the mineral medium described in (Pacaud et al. 1985).

When an acid is made by fermentation, the accumulated acid lowers the pH of the medium to a point at which the microorganism no longer grows, and acid production eventually stops. For this reason, it is necessary to add a reagent to the fermentation reaction which will neutralize, at least in part, the acid and maintain the pH at a sufficient level to permit the continued growth of the microorganism.

A commonly used neutralizing reagent is the basic solution of ammonia, whose chemical formula is $NH_3$.

Advantageously, during this culture step, fermentation broth is collected continuously, without interfering with the culture process, in particular without removing the biomass from the culture recipient.

Alternatively, the fermentation broth may be collected at certain time points, but also without interfering with the culture process.

According to these embodiments, the culture step is said "continuous".

Industrial and economic benefits from this implementation are a gain of time and raw materials, since the culture is in the starting phase only once; another benefit is a lower risk of contamination of the microorganism culture.

According to another embodiment of the invention, the process for producing organic acid salts is realized in batch or fed-batch conditions. In this case, the fermentation broth is collected at the end of culture.

Step (ii) of the Process: Pre-Treatment of the Fermentation Broth

The process according to the invention is characterized with a step (ii) of pre-treatment of the fermentation broth comprising at least the following substeps:
 a. Clarification step;
 c. Separation of organic acids by evaporation of the clarified fermentation broth and then condensation of the volatile fraction containing said organic acids (CVAF), and therefore elimination of non-volatile, solid impurities, mainly salts from the fermentation broth.

The clarification step (a) of the fermentation broth means clarifying the fermentation medium and removing the insoluble organic impurities from said fermentation medium. The clarification of the medium is carried out by any method known as such by those skilled in the art, which method is chosen, for example, from the group consisting of heating, flocculation, decanting, membrane techniques (microfiltration, ultrafiltration, diafiltration, nano-filtration and reverse osmosis) and centrifugation.

An optional step (b) of pH adjustment may be performed, consisting in adding mineral acids into the broth in order to lower the pH below the pKa of the organic acids contained in the broth, that are intended to be recovered.

This optional step is performed in order to maximize the proportion of organic acid(s) under their protonated form, and therefore to optimize their recovery in the condensed volatile fraction of the step (c).

This adjustment of the pH (acidification) is carried out by any method known by those skilled in the art, which method is chosen, for example, by adding mineral acids chosen from the group consisting of: sulfuric acid, nitric acid, phosphoric acid and chlorhydric acid.

The man skilled in the art knows the pKa of the different organic acid intended to be recovered, and is able to adjust the pH according to any pKa, for obtaining of pH of the clarified broth that is below the pKa of the organic acid intended to be recovered.

Table 1 below presents the pKa of a plurality of organic acids. This table lists the acid-base dissociation constants of organic compounds, including many amino acids. All data apply to dilute aqueous solutions and are presented in the form of pKa, which is the negative of the logarithm of the acid dissociation constant Ka.

TABLE 1 pKa of a plurality of organic acids

| Molecular formula | Name | $T_I$ ° C. | $pK_a$ |
|---|---|---|---|
| CH2O2 | Formic acid | 20 | 3.75 |
| C2HCl3O2 | Trichloroacetic acid | 25 | 0.70 |
| C2H2Cl2O2 | Dichloroacetic acid | 25 | 1.48 |
| C2H2O3 | Glyoxylic | 25 | 3.18 |
| C2H2O4 | Oxalic acid | 25 | 1.23 |
| C2H3BrO2 | Bromoacetic acid | 25 | 2.69 |
| C2H3ClO2 | Chloroacetic acid | 25 | 2.85 |
| C2H3IO2 | Iodoacetic acid | 25 | 3.12 |
| C2H4OS | Thioacetic acid | 25 | 3.33 |
| C2H4O2 | Acetic acid | 25 | 4.76 |
| C2H4O3 | Glycolic acid | 25 | 3.83 |
| C2H7AsO2 | Cacodylic acid | 25 | 1.57 |
| C3H3NO2 | Cyanoacetic acid | 25 | 2.45 |
| C3H4O2 | Acrylic acid | 25 | 4.25 |
| C3H4O3 | Pyruvic acid | 25 | 2.39 |
| C3H4O4 | Malonic acid | 25 | 2.83 |
| C3H5ClO2 | 2-Chloropropanoic acid | 25 | 2.83 |
| C3H5ClO2 | 3-Chloropropanoic acid | 25 | 3.98 |
| C3H6O2 | Propanoic acid | 25 | 4.86 |
| C3H6O3 | 3-Hydroxypropanoic acid | 25 | 4.51 |
| C3H6O3 | Lactic acid | 100 | 3.08 |
| C3H6O4 | Glyceric acid | 25 | 3.52 |
| C4H4N2O3 | Barbituric acid | 25 | 4.01 |
| C4H4N2O5 | Alloxanic acid | 25 | 6.64 |
| C4H4O4 | trans-Fumaric acid | 18 | 3.03 |
| C4H4O4 | Maleic acid | 25 | 1.83 |
| C4H4O5 | Oxaloacetic acid | 25 | 2.22 |

TABLE 1-continued pKa of a plurality of organic acids

| Molecular formula | Name | $T_I$ °C. | $pK_a$ |
|---|---|---|---|
| C4H6O2 | 3-Butenoic acid | 25 | 4.34 |
| C4H6O3 | Acetoacetic acid | 18 | 3.58 |
| C4H6O3 | 2-Oxobutanoic acid | 25 | 2.50 |
| C4H6O4 | Methymalonic acid | 25 | 3.07 |
| C4H6O4 | Succinic acid | 25 | 4.16 |
| C4H6O5 | Malic acid | 25 | 3.40 |
| C4H6O6 | a-Tartaric acid | 25 | 2.98 |
| C4H6O6 | meso-Tartaric acid | 25 | 3.22 |
| C4H6O8 | Dihydroxytartaric acid | 25 | 1.92 |
| C4H7NO2 | 4-Cyanobutanoic acid | 25 | 2.42 |
| C4H7NO4 | Aspartic acid | 25 | 1.99 |
| C4H8O2 | Butanoic acid | 25 | 4.83 |
| C4H8O2 | 2-Methylpropanoic acid | 25 | 4.88 |
| C4H8O3 | 3-Hydroxybutanoic acid | 25 | 4.70 |
| C4H8O3 | 4-Hydroxybutanoic acid | 25 | 4.72 |
| C4H9NO2 | 2-Aminobutanoic acid | 25 | 2.29 |
| C4H9NO2 | 4-Aminobutanoic acid | 25 | 4.03 |
| C5H4N4O3 | Uric acid | 12 | 3.89 |
| C5H6O4 | Itaconic acid | 25 | 3.85 |
| C5H8O4 | Glutaric acid | 25 | 4.31 |
| C6H10O4 | Adipic acid | 25 | 4.43 |
| C6H10O4 | 3-Methylglutaric acid | 25 | 4.24 |
| C6H11NO2 | l-Pipecolic acid | 25 | 2.28 |
| C7H14O2 | Heptanoic acid | 25 | 4.89 |
| C8H6O4 | o-Phthalic acid | 25 | 2.89 |
| C8H6O4 | Terephthalic acid | 25 | 3.51 |
| C8H14O4 | Octanedioic acid | 25 | 4.52 |

The step (c) is a step of separation by two successive steps of evaporation and condensation.

Firstly, the clarified fermentation both is heated in an evaporation unit in order to separate a gaseous part and a solid part. Operating parameters of evaporation unit are optimized for each treated clarified broth. Low pressures (<1 bara) can be applied, and temperature depends of pressure value (for example, at 500 mbara, temperature of the concentrate is about 110° C. for a particular *clostridium* fermentation broth). Depending on the targeted organic acids, the conditions might be adapted by the man skilled in the art to maximize the evaporation of said targeted organic acids in the volatile fraction.

Secondly, the gaseous, volatile part containing water, ammonium and organic acids is collected, while the solid, insoluble part containing impurities such as salts is eliminated.

The collected gaseous part is then condensed by refrigeration of the part, to obtain a liquid part hereafter designated as the condensed volatile acids fraction (CVAF).

In one embodiment, this step of separation can be realized by distillation, a process of separating the volatile components from the fermentation broth by selective evaporation and condensation, exploiting differences in the volatility of the broth's components. According to this embodiment, recovered organic acids would be selected among other volatile compounds, and the CVAF would comprise only organic acids and compounds of the same volatility than organic acids.

Other steps can be applied for the pre-treatment of the fermentation broth in order to improve the elimination of organic impurities. These steps are optional. They may be of particular importance when the fermentation broth contains a high quantity of alcohols. They include in particular substep(s) of distillation, in order to improve the recovery yield for organic acids (mainly used when the fermentation broth is a *Clostridium* broth), and/or reverse osmosis, in order to remove water and to concentrate organic acids.

Optional Step (iii)

It is understood that the method of the invention is defined with a sequence of at least four successive steps, but that optional, supplementary steps can be integrated in the sequence of the method.

In particular, supplementary step(s) can be performed right after the step (ii) of pre-treatment of the fermentation broth.

These optional steps are intended to increase the yield and purity of recovered organic acid salts, when the fermentation broth presents a high level of impurities or ammoniac.

As previously discussed, during the fermentation, the produced organic acids accumulate in the medium and lower the pH, to a point at which the microorganisms no longer grow. For this reason, a basic solution of ammonia or urea, or ammoniac gas, is added continuously during the fermentation for maintaining the pH at a sufficient level to permit the continued growth of microorganisms.

As a consequence, the fermentation broth may contain high level of ammoniac, transformed in an acid solution into ammonium cations $NH_4^+$.

In an embodiment of the invention, the method comprises a step (iii) of elimination of the ammonium cations present in the CVAF.

This step is carried out after step (ii) of pre-treatment of the fermentation broth, by passing the CVAF over a cation exchanger able to bind the ammonium cations, preferentially a strong cationic resin.

A "cationic resin treated fraction" is thus obtained.

Optional Step (iv)

In one embodiment of the invention, an optional step (iv) is performed in order to purify the organic acids contained into the CVAF or into the cationic resin treated fraction.

This step consists in passing the CVAF or cationic resin treated fraction from optional step (iii) over an anion exchanger, preferentially a strong anionic resin, able to bind the conjugate bases of the organic acids.

An anion exchanger is an ion-exchanger resin able to fix the conjugate bases (form A-) of the organic acids; the uncoupling (elution) of these conjugate bases is achieved with the addition of inorganic bases over said anion exchanger. The inorganic bases comprise anions (such as hydroxide) that will bind to the resin; and cations (such as sodium cations) that will complex with the conjugate bases, in the eluate fraction.

Step (v) of the Process: Addition of Inorganic Bases

After pre-treatment of the fermentation broth, the obtained CVAF is subjected to the addition of inorganic bases, to generate the organic acid salts.

If the optional step (iii) has been performed, the inorganic bases are added to the cationic resin treated fraction from the cation exchanger.

If the optional step (iv) has been performed, the inorganic bases are added to the anion exchanger where the conjugate bases are bound. Presence of inorganic bases will allow the elution of the conjugate bases under the form of organic acid salts.

The inorganic bases used to generate the organic acid salts are advantageously chosen among inorganic bases that are suitable for an oral administration to humans and/or animals.

The inorganic bases are preferably chosen among the group consisting of: salts of sodium, calcium, potassium, magnesium, and mixtures thereof.

The inorganic bases used to obtain organic acid salts are preferably chosen among the group consisting of: sodium hydroxide, calcium hydroxide, potassium hydroxide, magnesium hydroxide, sodium carbonates, calcium carbonates, potassium carbonates, magnesium carbonates, sodium oxides, calcium oxides, potassium oxides, magnesium oxides and mixtures thereof.

More preferentially, the added inorganic base is chosen among sodium hydroxide, sodium carbonate and sodium oxide.

In one embodiment of the invention, at least two different inorganic bases (i.e. a mixture) are added to the CVAF or to the cationic resin treated fraction or to the anion exchanger.

In one embodiment of the invention, only one inorganic base, chosen among the inorganic bases listed above, is added at the step (v) of the method.

According to this embodiment, the mixture of organic acid salts such as obtained by the method is composed of different organic acids, combined with a single cation: sodium, magnesium, potassium or calcium ions, preferentially with sodium ions.

In a preferred embodiment of the invention, the added inorganic base is sodium hydroxide (NaOH, consisting of sodium cations $Na^+$ and hydroxide anions $OH^-$).

It is understood that these inorganic bases are added in an efficient amount, i.e. in stoichiometric proportions necessary to transform the present quantity of organic acid into organic acid salts.

The man skilled in the art is able to determine the efficient amount of inorganic bases to be added to the CVAF or to the cationic resin treated fraction or to the anion exchanger, in function of the fraction volume. This quantity will also depend on the type of inorganic salt and on the type of cultivated microorganisms, and therefore of the major produced organic acid. Typical quantities of added inorganic bases are comprised between 5 grams to 500 grams per kilogram of CVAF.

Step (vi) of the Process: Eliminating the Remaining Water of the CVAF or the Cationic Resin Treated Fraction or the Eluate, and Recovering the Formed Organic Acid Salts The last fundamental step of the method according to the invention consists in recovering the organic acid salts from the CVAF or the cationic resin treated fraction or the eluate.

Since the organic acid salts are in a solution, a step of elimination of the remaining water is necessary.

Elimination of the remaining water can be carried out by any technique known by the man skilled in the art, such as drying, evaporation, vacuum dehydration, or uses of hygroscopic compounds.

This step (vi) may comprise one or more substep(s) chosen among the group consisting of: evaporation, atomization, granulation, agglomeration, crystallization, liquid/solid separation, filtration and centrifugation.

Evaporation refers to the removal of water in an evaporation unit. Pressure and temperature are controlled in order to distillate a part of the remaining water. The concentrate contains the organic acid slats, and the concentration is optimized regarding solubility of the different organic acid salts. This step is cost saving for the next ones.

Atomization designates the transformation of a liquid into a multiplicity of small drops. This transformation proceeds through the formation of disturbances on the surface of the liquid, followed by their amplification due to energy and momentum transfer from the surrounding gas.

Granulation refers to a process where the concentrated CVAF or fraction or eluate is processed in spray nozzles into a fluidized bed of powder. The powder could have be obtained by atomization or directly in the spray-granulator or recovered from a previous production. Solution of organic acids salts is pulverized on particle surface and heated air eliminates water, so that organic acid salts crystallize directly on the particle. Particle size will be controlled by variation of feed flow, spray nozzle air pressure, recycling rate of dry product and residence time in the equipment.

Agglomeration refers to a process where powder particles are made to adhere to form larger, multiparticle entities called granules. It is the process of collecting particles together by creating bonds between them. Bonds are formed by using a binding agent, preferably the organic acid salts solution. Solid particles of salts contained in the CVAF or the fraction or the eluate are agglomerated in order to create particles of organic acid salts. Agglomeration can be carried out by wet granulation or dry granulation, depending if it is carried out before or after the drying step.

A crystallization step consists in crystallizing the organic salts so as to recover the salts in solid form. This crystallization step can be carried out by means of technology chosen from the group consisting of crystallization by cooling, crystallization by evaporation-crystallization and adiabatic crystallization. Crystallization is usually followed with a step of centrifugation or filtration to separate the crystallized organic salts from the liquid.

The techniques of liquid/solid separation, filtration and centrifugation are intended to separate the organic acid salts when they are under the form of solid particles, for example after crystallization, from the remaining liquid of the CVAF or the fraction or the eluate.

It is understood that this last step (vi) can be performed according to any method known by the man skilled in the art, for the recovering of organic acid salts under a solid, dried form.

SPECIFIC EMBODIMENTS

Five schemes exemplifying the method of the invention are presented below. All these step sequences comprise the four necessary steps, and may also comprise some optional steps in their sequence.

Scheme 1

According to a specific embodiment of the invention, the method for producing organic acid salts comprises the successive steps of:
i) culturing a microorganism in an appropriate culture medium comprising a carbon source and a nitrogen source, during a sufficient time to obtain a fermentation broth comprising organic acids;
ii) pre-treating said fermentation broth with at least the following steps:
clarification of the fermentation broth; and
separation of organic acids by evaporation of the clarified fermentation broth and then condensation of the volatile fraction containing said organic acids, hereafter designated as the condensed volatile acids fraction (CVAF);
v) adding inorganic bases to said CVAF, preferably sodium hydroxide;
vi) atomization or granulation or crystallization; and drying and/or evaporating the formed organic acid salts.

Figure 1:
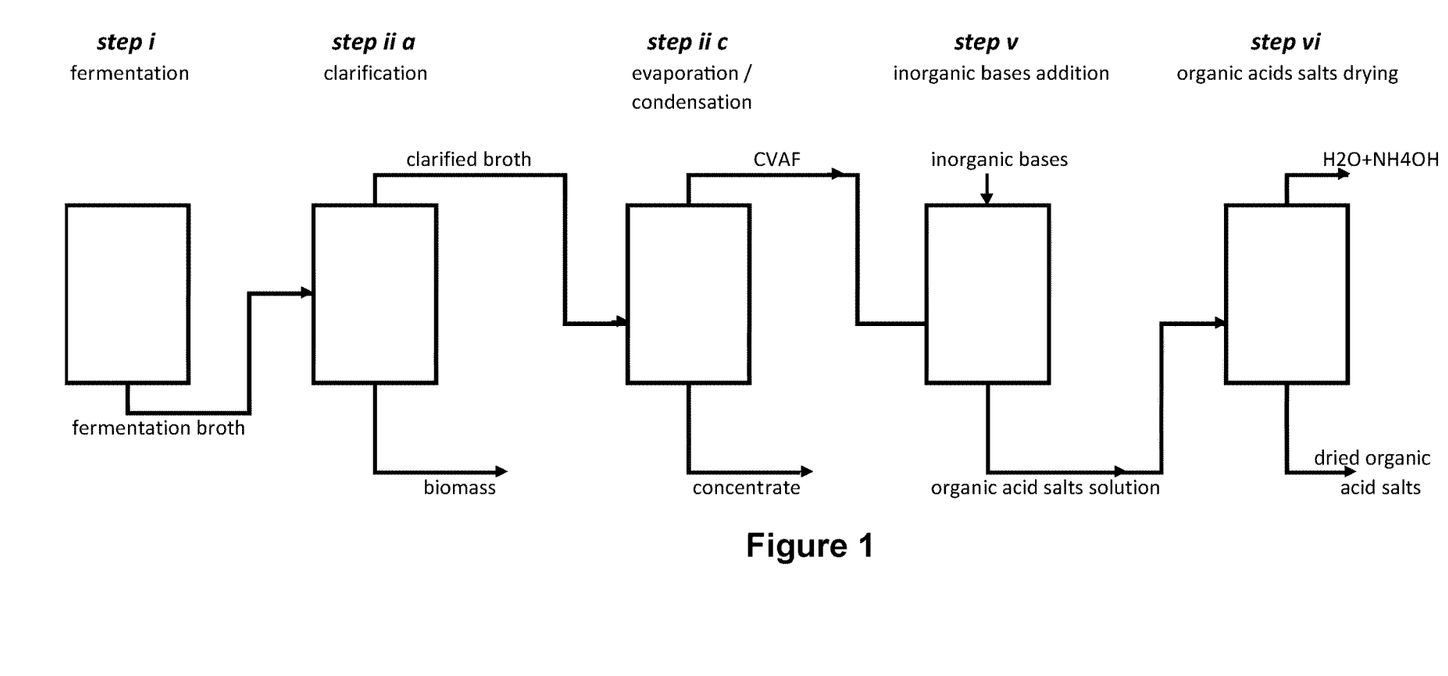
FIG. 1. Schematic representation of the steps included in the process according to scheme 1
FIG. 2. Schematic representation of the steps included in the process according to scheme 2
FIG. 3. Schematic representation of the steps included in the process according to scheme 3
FIG. 4. Schematic representation of the steps included in the process according to scheme 4
FIG. 5. Schematic representation of the steps included in the process according to scheme 5

In this scheme presented in FIG. 1, the step (vi) of elimination of water is adjusted in order to optimize the final render of the product. In one embodiment of the invention, this step comprises an atomization or granulation of the organic acid salts.

Advantageously, the step of elimination of water might be carried out by the technique of crystallization followed with a liquid/solid separation, or a centrifugation, before a final drying.

It is understood that a substep of filtration might also be introduced during the process, in order to separate the crystalline material, instead of centrifugation or liquid/solid separation.

According to a specific embodiment of the invention, the method for producing organic acid salts consists in the successive steps listed in scheme 1.

Scheme 2

According to a specific embodiment of the invention, the method for producing organic acid salts comprises the successive steps of:
i) culturing a microorganism in an appropriate culture medium comprising a carbon source and a nitrogen source, during a sufficient time to obtain a fermentation broth comprising organic acids;
ii) pre-treating said fermentation broth with at least the following steps:
clarification of the fermentation broth; and
separation of organic acids by evaporation of the clarified fermentation broth and then condensation of the volatile fraction, hereafter designated as the condensed volatile acids fraction (CVAF);
iv) passing the CVAF over an anion exchanger, preferentially over a strong anionic resin;
v) adding inorganic bases to the anion exchanger to eluate the bound conjugate bases of said organic acids, and obtaining an eluate containing said conjugate bases;
vi) evaporation of the eluate, then atomization or granulation or crystallization, then centrifugation and drying in order to collect the formed organic acid salts.

Figure 2:
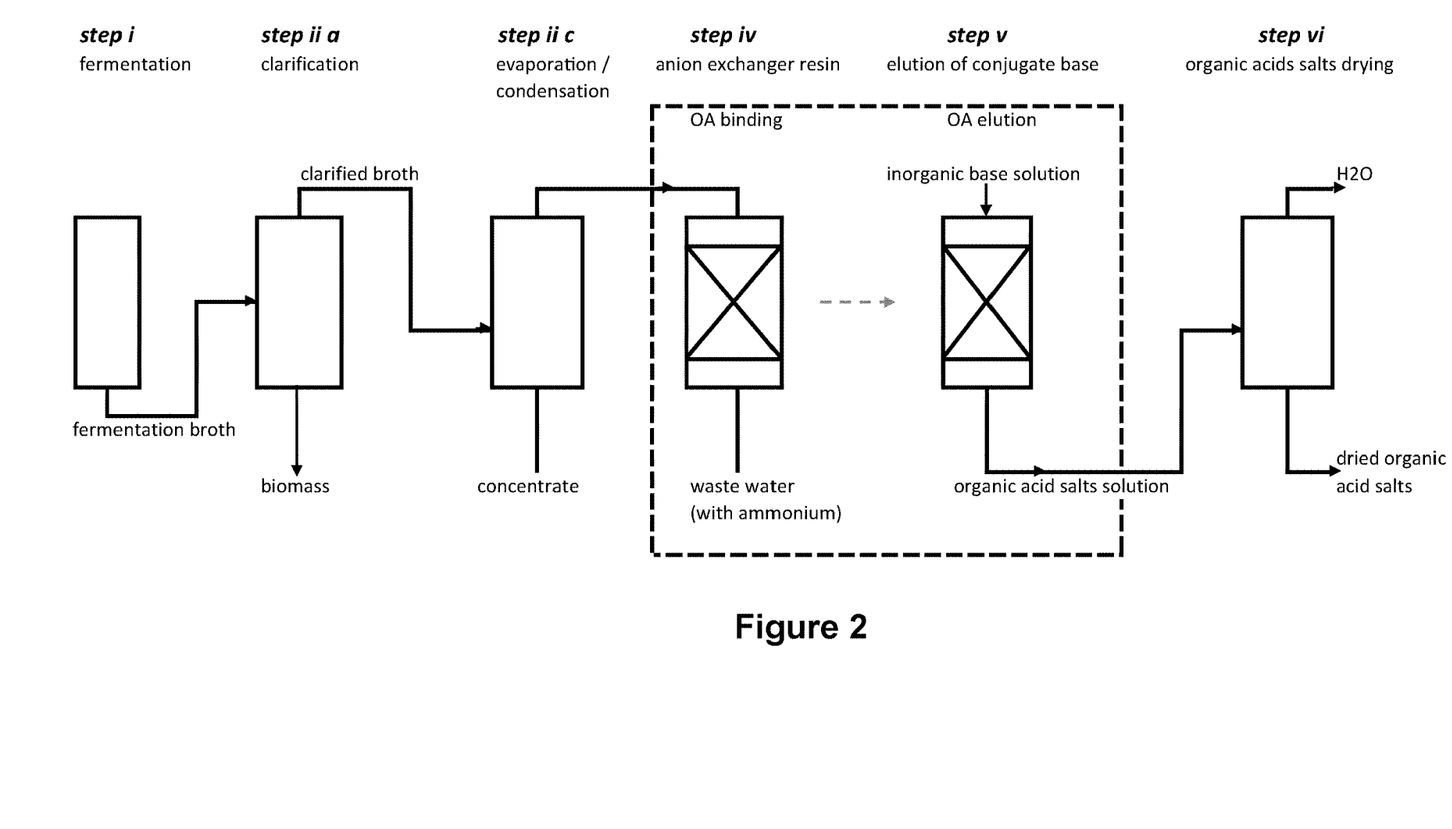

This scheme is schematically represented in FIG. 2.

Preferably, a strong anionic resin is used, because of the high level of ammonium cations that may interfere with the binding of the conjugate bases on the anionic resin.

According to a specific embodiment of the invention, the method for producing organic acid salts consists in the successive steps listed in scheme 2.

Scheme 3

According to a specific embodiment of the invention, the method for producing organic acid salts comprises the successive steps of:
i) culturing a microorganism in an appropriate culture medium comprising a carbon source and a nitrogen source, during a sufficient time to obtain a fermentation broth comprising organic acids;
ii) pre-treating said fermentation broth with at least the following steps:
clarification of the fermentation broth; and
separation of organic acids by evaporation of the clarified fermentation broth and then condensation of the volatile fraction, hereafter designated as the condensed volatile acids fraction (CVAF);
iii) eliminating the ammonium cations present in the CVAF, by passing the CVAF over a cation exchanger, to bind the ammonium cations;
iv) passing the cationic resin treated fraction obtained in step (iii) over an anion exchanger;
v) adding inorganic bases to the anion exchanger to eluate the bound conjugate bases;
vi) evaporation of the eluate, then atomization or granulation or crystallization, then centrifugation and drying in order to collect the formed organic acid salts.

The cation exchanger is an ion-exchanger resin able to fix the ammonium cations ($NH_4^+$) present in the CVAF; the obtained cationic resin treated fraction, after passage through the resin, comprises the conjugate bases of the organic acids. The cationic resin is preferentially a strong cationic resin.

In step (iv), the cationic resin treated fraction is passed over an anion exchanger able to fix the conjugate bases (form A-) of the organic acids; the uncoupling (elution) of these conjugate bases can be achieved with the addition of inorganic bases, comprising anions (such as hydroxide) that will be fixed to the ion exchanger; and cations (such as sodium cations) that will complex with the conjugate bases, in the eluate fraction.

Figure 3:
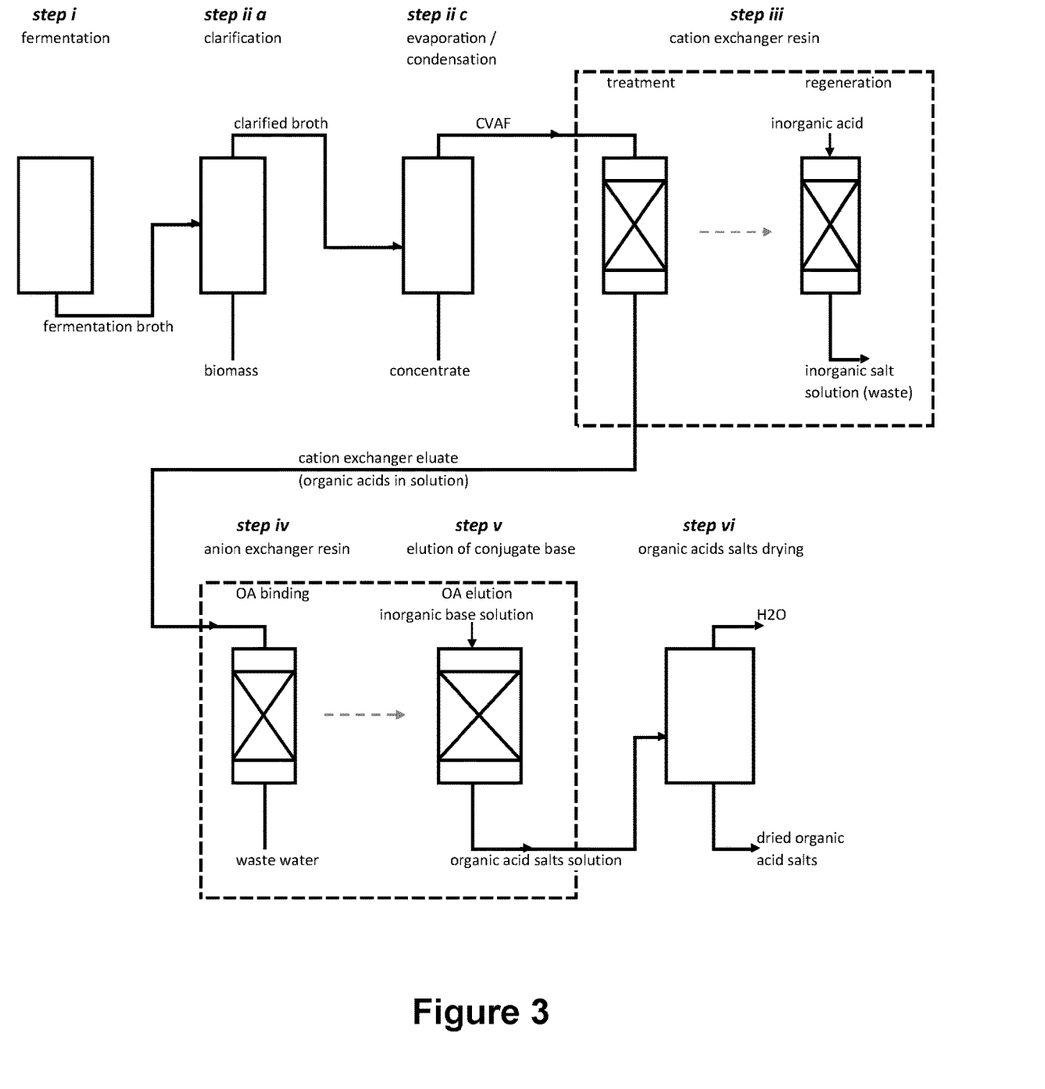

In this scheme, presented in FIG. 3, the anion exchanger is indifferently a strong or a weak anionic resin, since the ammonium cations have been previously eliminated.

According to a specific embodiment of the invention, the method for producing organic acid salts consists in the successive steps listed in scheme 3.

Scheme 4

According to a specific embodiment of the invention, the method for producing organic acid salts comprises the successive steps of:
i) culturing a microorganism in an appropriate culture medium comprising a carbon source and a nitrogen source, during a sufficient time to obtain a fermentation broth comprising organic acids;
ii) pre-treating said fermentation broth with at least the following steps:
clarification of the fermentation broth; and
separation of organic acids by evaporation of the clarified fermentation broth and then condensation of the volatile fraction, hereafter designated as the condensed volatile acids fraction (CVAF);
iii) eliminating the ammonium cations from the CVAF by passing the pH-adjusted CVAF over a cation exchanger;
v) adding inorganic bases to the cationic resin treated fraction;
vi) eliminating the remaining water of the cationic resin treated fraction, and collecting the formed organic acid salts.

Figure 4:
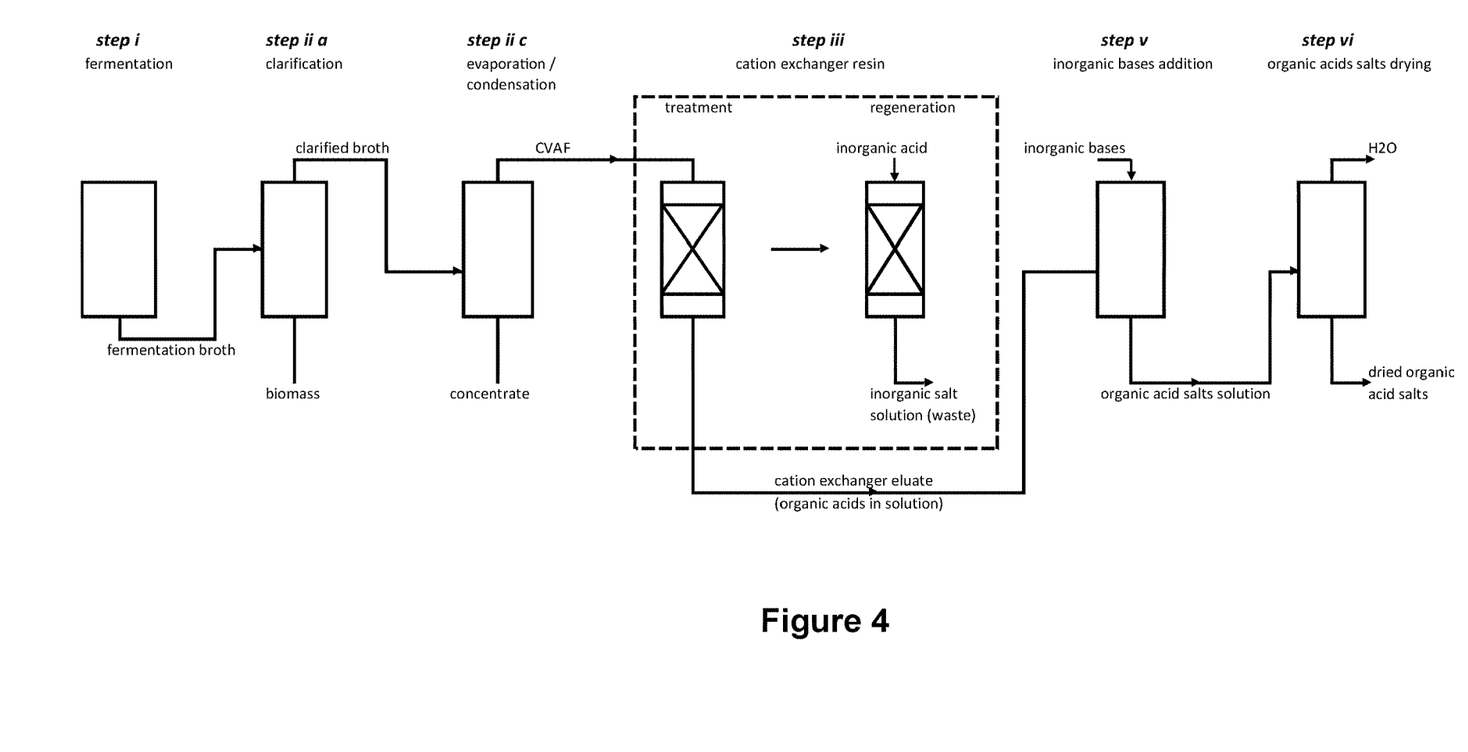

This scheme is schematically represented in FIG. 4.

The cation exchanger is an ion-exchanger resin able to fix the ammonium cations ($NH_4^+$) present in the CVAF; the obtained cationic resin treated fraction, after passage through the resin, comprises the conjugate bases of the organic acids. The cationic resin is preferentially a strong cationic resin.

According to a specific embodiment of the invention, the method for producing organic acid salts consists in the successive steps listed in scheme 4.

Scheme 5

According to another specific embodiment of the invention, the method for producing organic acid salts consists in the successive steps of:
i) culturing a microorganism in an appropriate culture medium comprising a carbon source and a nitrogen source, during a sufficient time to obtain a fermentation broth comprising organic acids;
ii) pre-treating said fermentation broth with at least the following steps:
clarification of the fermentation broth; and
separation of organic acids by evaporation of the clarified fermentation broth and then condensation of the volatile fraction, hereafter designated as the condensed volatile acids fraction (CVAF);
eliminating the ammonium cations from the CVAF by adding a mineral acid and then evaporation-crystallization of the pH adjusted CVAF, organic acids will be recovered in condensed distillates (DCVAF for double condensed volatile acid fraction) and inorganic base formed from ammonium will be recovered by centrifugation/drying of the crystals;

v) adding inorganic bases to said DCVAF;

vi) eliminating the remaining water of the DCVAF, and recovering the formed organic acid salts.

Figure 5:
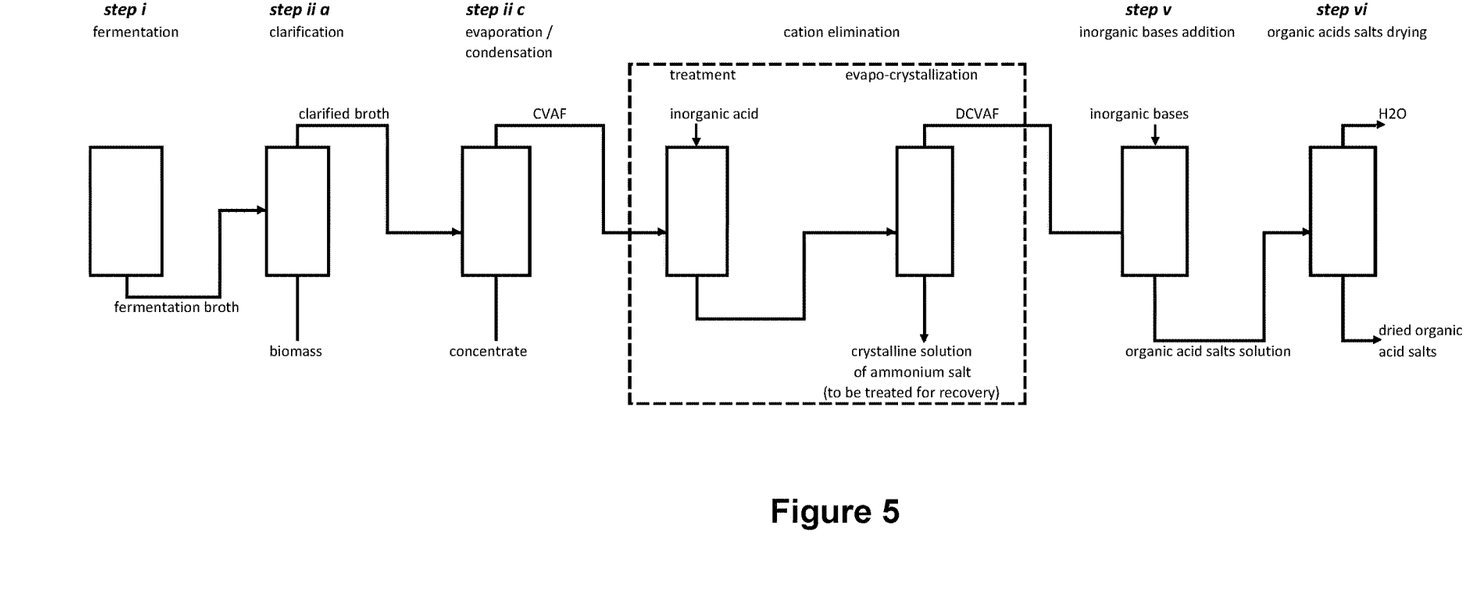

In this scheme 5, presented in FIG. 5, an optional step of addition of a mineral (inorganic) acid is performed between steps (ii) and (v).

Addition of a mineral acid, such as nitric acid, sulfuric acid, and phosphoric acid, is made in a stoichiometric quantity with ammonium cations in order to generate ammonium salts. This step allows the neutralization of the pH of the CVAF: pH is then low, so that organic acids are in proton form AH.

In a preferred embodiment of the invention, the mineral acid is sulfuric acid.

The following step of evaporation-crystallization is performed in order to recover the volatile organic acids in the gaseous part (DCVAF), and to separate the ammonium salts that are contained in the crystalline material. Said crystalline material can be treated by filtration and drying in order to recover organic acids that were lost in the first distillation step directly valuable ammonium salts instead of waste water.

The DCVAF is then processed according to steps (v) and (vi) as described previously.

Specific Combinations

In a first embodiment, the method according to this invention is a method for producing butyric acid salts.

According to a specific embodiment of the invention, the method for producing butyric acid salts comprises culturing a microorganism of the family Clostridiaceae, preferentially from the species *Clostridium acetobutylicum*.

According to a more specific embodiment of the invention, the method is intended for producing butyric acid sodium salts.

In a second embodiment, the method according to this invention is a method for producing acetic acid salts, or a method for producing acetic acid and butyric acid salts.

According to a specific embodiment of the invention, the method for producing acetic acid and butyric acid salts comprises culturing a microorganism of the family Eubacteriaceae, preferentially of the species *Eubacterium limosum*.

In a third embodiment, the method according to this invention is a method for producing glycolic acid salts.

According to a specific embodiment of the invention, the method for producing glycolic acid salts comprises culturing a microorganism of the family Enterobacteriaceae, preferentially of the species *Escherichia coli*.

According to a specific embodiment of the invention, the method for producing glycolic acid salts comprises culturing a microorganism of the family *Saccharomyces*, preferentially of the species *Pichia kudriavzevii*.

In a fourth embodiment, the method according to this invention is a method for producing lactic acid salts, comprising culturing at least one lactic acid-producing microorganism.

In a fifth embodiment, the method according to this invention is a method for producing propionic acid salts, comprising culturing at least one propionic acid-producing microorganism.

In a sixth embodiment, the method according to this invention is a method for producing valeric acid salts, comprising culturing at least one valeric acid-producing microorganism.

In a seventh embodiment, the method according to this invention is a method for producing acetic acid salts, comprising culturing at least one acetic acid-producing microorganism.

Organic Acid Salts Such as Obtained

The method of the invention does not comprise a selection step of particular organic acid salts. Therefore, the produced organic acid salts are recovered under the form of a mixture of at least two different organic acid salts.

The present invention concerns a mixture of organic acid salts such as obtained by the method as described previously.

These organic acid salts are composed of conjugate bases of organic acids, and inorganic cations such as sodium, magnesium, potassium or calcium cations.

In a preferred embodiment, this mixture of organic acid salts is exclusively composed of salts comprising one single type of cations, preferentially sodium cations. For example, the mixture as obtained shall comprise butyric acid sodium salts, and acetic acid sodium salts.

In another preferred embodiment, this mixture of organic acid salts comprises a major component, meaning that the weight of said major component represents more than 50% of the mixture weight.

In another preferred embodiment, this mixture of organic acid salts comprises at least two major components, meaning that the weight of said major components represents more than 50% of the mixture weight.

Evaluation of the weight of each component of the mixture can be carried out by the man skilled in the art, after isolation of each organic acid salt present in the mixture, by usual techniques such as HPLC and mass spectroscopy.

The proportion of each recovered organic acid depends, at least, on the cultivated microorganism and on the time of fermentation of said microorganism.

In a particular embodiment of the invention, the major component of the mixture is butyric acid salts and derivatives thereof.

Preferentially, these butyric acid salts and derivatives thereof are butyric acid sodium salts.

In another embodiment of the invention, the major components of the mixture are butyric acid salts and acetic acid salts, and derivatives thereof, preferentially butyric acid sodium and acetic acid sodium salts.

In another embodiment of the invention, the major component of the mixture is glycolic acid salts and derivatives thereof, preferentially glycolic acid sodium salts.

EXAMPLES

The present invention is further defined in the following examples. It should be understood that these examples, while indicating preferred embodiments of the invention, are given by way of illustration only. From above disclosure and these examples, the man skilled in the art can make various changes of the invention to adapt it to various uses and conditions without modify the essentials means of the invention.

Example 1: Recovery of Organic Acids Salts from Fermentation Broth of 1,3-Propanediol Production with *Clostridium acetobutylicum* Strains

*Clostridium acetobutylicum* recombinant strains are fermented in continuous fermenter to produce 1,3-propanediol as described in patent applications EP 2 427 562, EP 2 638 172 and non-published yet EP 17305187.1.

Several organic acids produced during the fermentation run are considered as by-products as for instance; butyric acid, formic and acetic acids. Typical composition of fermentation broth is given below, after the process step (i) of fermentation.

TABLE 2 typical composition of a fermentation broth issued from step i.

| Compound | Titer (g/kg) | Relative purity (%) |
|---|---|---|
| Biomass | 0.20 ± 0.05 | 0.3% |
| Glycerol (residual) | 1.2 ± 0.6 | 1.5% |
| 1,3-propanediol | 51.8 ± 1.8 | 67.4% |
| Butyric acid | 11.7 ± 0.6 | 15.2% |
| Acetic acid | 2 ± 0.6 | 2.6% |
| Formic acid | 0.2 ± 0.1 | 0.3% |
| Salts | 9.5 ± 0.5 | 12.4% |

After clarification of the fermentation broth (step ii.a.), the composition has almost not change, as only biomass has been eliminated from the fermentation broth.

Step (ii.c) is performed in order to separate volatile organic acids, using more than one stages of evaporation and condensation, plus a reverse osmosis step of some condensates. The CVAF obtained at the end of step ii.c is about the following composition.

TABLE 3

Typical composition of the CVAF after step (ii.c).

| Compound | Titer (g/kg) | Relative purity (%) | Purity increase vs broth |
|---|---|---|---|
| Biomass | 0 | 0% | 0 |
| Glycerol (residual) | 0.1 | 0.1% | x 0.07 |
| 1,3-propanediol | 4.9 | 6% | x 0.09 |
| Butyric acid | 52.7 | 64.4% | x 4.2 |
| Acetic acid | 10.4 | 12.7% | x 4.9 |
| Formic acid | 1 | 1.2% | x 3.9 |
| Ammonium | 12.7 | 15.5% | nd |

Purity of volatile organic acid has been increased approximately 4 times regarding the composition of the fermentation broth.

No optional step (among iii and iv) is performed on this CVAF.

Step (v) of addition of inorganic acid is performed by addition of soda (sodium bicarbonate). The amount of soda is 32 g/kg of CVAF, in order to obtain a stoichiometric ratio soda/organic acids.

Step (vi): this solution was then concentrated by evaporation. A falling film evaporator was used at atmospheric pressure, and temperature of the final concentrate was about 112° C. Water and ammonia were recovered in the distillates, while both organic acids sodium salts were recovered in the concentrate. The composition of the concentrate is given in the table below.

TABLE 4 typical composition of the concentrate

| Compound | Titer (g/kg) | Relative purity (%) | Purity increase vs broth |
|---|---|---|---|
| Glycerol (residual) | 0.3 | 0.1% | x 0.05 |
| 1,3-propanediol | 20.5 | 4.6% | x 0.07 |
| Butyric acid | 271.1 | 61.2% | x 4.0 |
| Acetic acid | 54.4 | 12.3% | x 4.7 |
| Formic acid | 5.1 | 1.2% | x 3.8 |
| Sodium | 91.3 | 20.6% | nd |
| Ammonium | <1 | nd | nd |

By replacing ammonium by sodium, global dry matter content increased, so that relative purities decreased. After this step, the composition in sodium salts is shown below in table 5.

TABLE 5 typical composition of sodium salts of the concentrate

| Compound | Titer (g/kg) | Relative purity (%) |
|---|---|---|
| 1,3-propanediol | 20.5 | 4.6% |
| Sodium Butyrate | 338.9 | 76.8% |
| Sodium Acetate | 74.4 | 16.9% |
| Sodium Formate | 7.5 | 1.7% |

This concentrate was then processed on a fluidized bed dryer using spray granulation nozzle. The equipment used was a Procell Labsystem from Glatt®. Heated air was used to dry the product while organic acids sodium salts solution was sprayed in the chamber. A classification system was used at outlet of the equipment in order to optimize particle size distribution of the dry product.

TABLE 6

Typical final composition in organic acid salts

| Compound | Titer (g/kg) | Relative purity (%) |
|---|---|---|
| 1,3-propanediol | 0 | 0% |
| Sodium Butyrate | 801 | 79.6% |
| Sodium Acetate | 173 | 17.2% |
| Sodium Formate | 17.9 | 1.8% |
| Water | 14.7 | 1.5% |

Particle size distribution of dry product was measured using a Mastersizer 3000 (Malvern®) that showed that the product has a thin profile, and a good mechanic resistance under air pressure.

The table below gives the composition of dry product using organic acid concentrations, so that relative purities can be compared to broth composition.

TABLE 7

Typical composition of dry product using organic acid concentrations

| Compound | Titer (g/kg) | Relative purity (%) | Purity increase vs broth |
|---|---|---|---|
| Butyric acid | 640.8 | 63.7% | x 4.2 |
| Acetic acid | 126.6 | 12.6% | x 4.9 |

TABLE 7-continued

Typical composition of dry product
using organic acid concentrations

| Compound | Titer (g/kg) | Relative purity (%) | Purity increase vs broth |
|---|---|---|---|
| Formic acid | 12.1 | 1.2% | x 3.9 |
| Sodium | 212.4 | 21.1% | |

By applying the main steps of the invention, a dry product containing organic acid sodium salts had been obtained, with a purity increased about 4 times regarding the initial composition of the fermentation broth.

Example 2: Recovery of Pure Sodium Butyrate Salt from a Fermentation Broth of 1,3-Propanediol Production with Clostridium acetobutylicum Strains The process according to the invention can allow production of a specific organic salt, from a pure solution of said specific organic acid, as for instance butyric acid.

The fermentation broth from Clostridium acetobutylicum strains is pre-treated according to step (ii). The CVAF is then submitted to a purification process to recover pure butyric acid.

Step (v) of the process (addition of inorganic bases, in particular sodium salts) is then performed, so that a solution of pure sodium butyrate is obtained, and then processed in step (vi), using the same drying equipment as described in example 1.

The dried product obtained by spray granulation has a sodium butyrate content of 98.5% (1.5% water). The composition is given in table 8 below.

TABLE 8

Composition of sodium butyrate salt

| Compound | Titer (g/kg) | Relative purity (%) | Purity increase vs broth |
|---|---|---|---|
| Butyric acid | 788 | 78.8 | x 5.2 |
| Sodium | 197 | 19.7% | |

The pure sodium butyrate obtained is a white powder composed of small spherical balls.

Particle size distribution of dry product was measured using a Mastersizer 3000 (Malvern®) that showed that the product has a thin profile, and a good mechanic resistance under air pressure.

This example shows that the process of the invention may comprise supplementary purification steps, and that in that case the purity of the product can be improved from the same fermentation broth. The purity of the butyric acid has been increased more than 5-times regarding its initial purity in liquid broth (vs 4-times in example 1).

REFERENCES

Patents

EP 1 094 054
EP 350 355
U.S. Pat. No. 4,490,295
US 2004/0048344
US 2004/0077057
U.S. Pat. No. 3,720,584
CN 101475464
WO 2013/169447

Non-Patents

Anderson, 1946, *Proc. Natl. Acad. Sci. USA* 32:120-128.
Miller, 1992, Laboratory Manual and Handbook for *Escherichia coli* and Related Bacteria, Cold Spring Harbor Laboratory Press, Cold Spring Harbor, N.Y.
Schaefer et al. 1999, *Anal. Biochem.* 270: 88-96.
Zhao X, Condruz S, Chen J, Jolicoeur M. *A quantitative metabolomics study of high sodium response in Clostridium acetobutylicum ATCC 824 acetone-butanol-ethanol (ABE) fermentation*. Scientific Report. 2016 Jun. 20; 6:28307
S Pacaud, P Loubiere, G Goma. *Methanol metabolism by Eubacterium limosum B2: Effects of pH and carbon dioxide on growth and organic acid production*. Current Microbiology, Vol 12, 1985.

The invention claimed is:

1. A method for producing organic acid salts comprising at least the successive steps of:
   i) culturing a microorganism in an appropriate culture medium comprising a carbon source and a nitrogen source, during a sufficient time to obtain a fermentation broth comprising organic acids;
   ii) pre-treating said fermentation broth with at least the following steps:
      a. clarification of the fermentation broth, for removing the insoluble organic impurities;
      b. optionally, adjustment of the pH of the clarified fermentation broth; and
      c. separation of organic acids by evaporation of the clarified fermentation broth and then condensation of the volatile fraction containing said organic acids, hereafter designated as the condensed volatile acids fraction (CVAF);
   iii) optionally, passing the CVAF over a cation exchanger able to bind ammonium cations;
   iv) optionally, passing the CVAF or the cationic resin treated fraction over an anion exchanger able to bind conjugate bases of the organic acids;
   v) adding inorganic bases to said CVAF or to said cationic resin treated fraction or to said anion exchanger to eluate bound conjugate bases;
   vi) eliminating the remaining water of the CVAF or of the cationic resin treated fraction or of the eluate, this step being carried out by any technique chosen among the group: drying, evaporation, vacuum dehydration and uses of hygroscopic compounds, and recovering the formed organic acid salts,
      wherein the organic acid salts are chosen among the group consisting of: salts of butyric acid, lactic acid, propionic acid, valeric acid, acetic acid, glycolic acid, sorbic acid, fumaric acid, formic acid, malic acid, tartaric acid, citric acid, derivatives of said organic acids and mixtures thereof.

2. The method according to claim 1 wherein said microorganism is a bacterium.

3. The method according to claim 2 wherein said microorganism is a *Clostridium acetobutylicum* bacterium.

4. The method according to claim 2 wherein said microorganism is a bacterium chosen among the group consisting of: *Escherichia coli, Bacillus subtilis, Corynebacterium glutamicum, Clostridium acetobutylicum, Clostridium pasteurianum* and *Eubacterium limosum*.

5. The method according to claim 1 wherein said microorganism is a yeast.

6. The method according to claim 5 wherein said microorganism is chosen among the group consisting of: *Saccharomyces cerevisiae, Pichia kudriavzevii* and *Kluyveromyces lactis*.

7. The method according to claim 1 wherein the step (ii) of pre-treatment comprises one or more sub-steps of distillation and/or reverse osmosis.

8. The method according to claim 1 wherein in step (v), the added inorganic bases are chosen among the group consisting of: salts of sodium, calcium, potassium, magnesium, and mixtures thereof.

9. The method according to claim 8 wherein in step (v), the added inorganic bases are chosen among the group consisting of: sodium hydroxide, sodium carbonate and sodium oxide.

10. The method according to claim 9 wherein the added inorganic base is sodium hydroxide.

11. The method according to claim 1 wherein the step (vi) of eliminating the remaining water comprises one or more sub-steps chosen among the group consisting of: evaporation, atomization, granulation, agglomeration, crystallization, liquid/solid separation, filtration and centrifugation.

* * * * *